United States Patent [19]

Hedrich

[11] 4,201,569
[45] May 6, 1980

[54] 2,3-DISUBSTITUTED ARALKYLAMINOACRYLONITRILES AND USE AS HERBICIDES

[75] Inventor: Loren W. Hedrich, Overland Park, Kans.

[73] Assignee: Gulf Oil Corporation, Pittsburgh, Pa.

[21] Appl. No.: 13,779

[22] Filed: Feb. 21, 1979

Related U.S. Application Data

[63] Continuation-in-part of Ser. No. 838,523, Oct. 3, 1977, Pat. No. 4,154,599.

[51] Int. Cl.$^2$ .................... A01N 9/20; C07C 121/78
[52] U.S. Cl. .................................. 71/98; 260/465 D; 260/465.4; 424/304
[58] Field of Search ...................... 260/465 D; 71/98

[56] References Cited

U.S. PATENT DOCUMENTS

| | | | |
|---|---|---|---|
| 3,723,498 | 3/1973 | Joos | 71/98 |
| 3,865,863 | 2/1975 | Field et al. | 260/465 E |
| 4,154,599 | 5/1979 | Hedrich | 71/98 |

*Primary Examiner*—Dolph H. Torrence
*Attorney, Agent, or Firm*—Carl A. Cline

[57] ABSTRACT

New compounds which are useful as herbicides and fungicides have the general structural formula

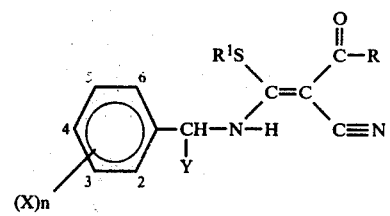

in which R is $C_1$ to $C_4$ straight chain saturated or unsaturated alkoxy, amino, dimethylamino or straight chain $C_1$ to $C_3$ monoalkylamino, $R^1$ is methyl or ethyl, X is nitro, methoxy, methyl, ethyl, Br, Cl or F in which n is an integer from 0 to 2, at least one of the 2 and 6 positions is unsubstituted and Y is H or a $C_1$ to $C_5$ branched or unbranched, saturated or unsaturated alkyl or cycloalkyl substituent group.

29 Claims, No Drawings

2,3-DISUBSTITUTED ARALKYLAMINOACRYLONITRILES AND USE AS HERBICIDES

This is a continuation-in-part of U.S. patent application Ser. No. 838,523 filed Oct. 3, 1977 now U.S. Pat. No. 4,154,599.

DESCRIPTION OF THE INVENTION

In U.S. Pat. No. 3,865,863 there is disclosed a class of herbicidal compounds having the general structural formula:

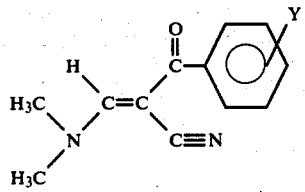

However, many acyl and carbamyl derivatives of acrylonitrile are completely non-phytotoxic or possess no practical utility for this purpose. In U.S. Ser. No. 838,523 there are disclosed several novel acyl and carbamyl-substituted acrylonitrile compounds which have no substantial utility as herbicides and for which no other utility is disclosed. A limited class of novel compounds which are useful as herbicides is disclosed, however. These compounds have the general structural formula

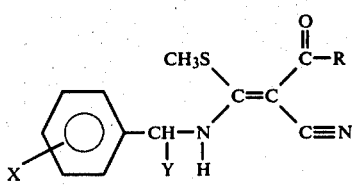

in which R is methoxy, amino, dimethylamino or straight chain $C_1$ to $C_3$ monoalkylamino, X is hydrogen, nitro, methoxy, methyl, chloro or fluoro, located in either or both meta and para positions and Y is hydrogen or methyl.

I have now discovered that the class of novel herbicides extends beyond the limits previously disclosed in U.S. Ser. No. 838,523 and furthermore, many of the novel compounds are also useful as agricultural fungicides. These compounds have the general structural formula

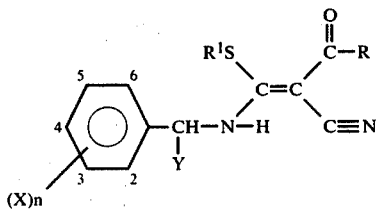

in which R is $C_1$ to $C_4$ straight chain saturated or unsaturated alkoxy, amino, dimethylamino or straight chain $C_1$ to $C_3$ monoalkylamino, $R^1$ is methyl or ethyl, X is nitro, methoxy, methyl, ethyl, Br, Cl or F in which n is an integer from 0 to 2, at least one and preferably both of the 2 and 6 positions is unsubstituted and Y is H or a $C_1$ to $C_5$ branched or unbranched, saturated or unsaturated alkyl or cycloalkyl substituent group.

Preparation of the Novel Compounds

Starting materials were prepared according to Gompper and Toepfl, Chem. Ber., 95, 2861 (1962). These include 2-cyano-3, 3-bismethylthioacrylate having the structural formulas,

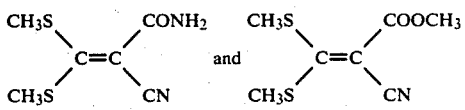

prepared from the corresponding cyanoacetyl compounds. The substituted benzylamine starting materials were purchased or made by means of the Leuckart Wallach reaction, Organic Reactions, vol. 5, page 301 (1949).

General procedures for the preparation of substituted cyanoacetamides and for the final products are illustrated below:

(a) Preparation of Substituted 2-Cyanoacetamides

A mixture of 25 mmol of the desired amine and 25 mmol of methyl cyanoacetate in 50 ml of methanol was refluxed overnight. On cooling the solids crystallized and were removed by filtration. In the case of liquid products the solvent was distilled under reduced pressure.

Various cyanoacetate esters are available commercially or may be made by customary ester synthesis methods. Both cyanoacetamides and cyanoacetate esters may be converted to bis alkylthio acrylates, as illustrated in the following procedures.

(b) Preparation of Allyl 2-cyano-3, 3-dimethylthioacrylate

A solution of 8.8 g (0.22 g-at.) of sodium hydroxide in 100 ml of water was placed in a 500 ml three-necked, round-bottomed flask equipped with a reflux condenser, mechanical stirrer and thermometer. To this was added a solution of 100 ml of dichloromethane containing 7.4 g (20 mmol) of tetra-n-butylammonium iodide and 12.5 g (0.1 mol) of allyl cyanoacetate. Carbon disulfide (9.1 g, 0.12 mol) in 25 ml of dichloromethane was added dropwise with stirring while maintaining the temperature below 25°. A mild exotherm was noted. The two-phase solution was stirred at room temperature for two hours. Dimethylsulfate (27.7 g, 0.22 mol) was added dropwise at a rate slow enough to keep the temperature below 25°. Following the addition the mixture was stirred for three hours at room temperature. The organic layer was transferred to a separatory funnel and washed twice with water and once with saturated solution of sodium chloride and dried over anhydrous magnesium sulfate.

Following filtration the solvent was distilled and the residue was slurried with 400 ml of ether. The precipitated tetra-n-butylammonium salt was removed by filtration and the ether distilled affording 15.8 g of liquid residue, IR and NMR spectra were consistent with the desired product. The product was used without further purification since decomposition resulted on attempted distillation.

(c) Preparation of n-Butyl 2-cyano-3, 3-dimethylthioacrylate

A solution of n-butyl cyanoacetate (69.5 g, 0.49 mol) in 200 ml of dimethylformamide was placed in a one liter three-necked, round-bottomed flask equipped with a thermometer, dropping funnel, and magnetic stirrer. To this was added 101 g (0.73 g-at.) of anhydrous potassium carbonate with rapid stirring. Carbon disulfide (41.2 g, 0.54 mol) was added over a two hour period resulting in a rise in temperature to 35°. The mixture was stirred at room temperature for 2.5 hours followed by heating on a steam bath for one hour. Dimethyl sulfate (68.1 g, 0.54 mol) was added dropwise with the temperature maintained at 20° by means of an ice-bath. Following the addition the mixture was stirred overnight at room temperature. The mixture was filtered and the filtrate concentrated to the greatest extent possible on a rotary evaporator and poured into one liter of ice-water. The aqueous mixture was extracted with 800 ml of ether and the ether extracts combined and washed with saturated solution of sodium chloride and dried over anhydrous magnesium sulfate. The mixture was filtered, the solvent distilled and the traces of ether removed with high vacuum affording 106 g of crude product. IR and NMR spectra were consistent with the desired product. The product was used without further purification because of decomposition on attempted distillation.

(d) Preparation of 2,3,3-trisubstituted acrylonitriles

A mixture of the 2-cyano-3, 3-bisalkylthioacrylamide or acrylate and an equimolar portion of the desired amine (20–25 mmol of each) in 50 ml ethanol was refluxed overnight. A 10% NaOH solution was used to trap the methyl mercapton evolved. Solids crystallized on cooling. Liquid products, usually oils which decomposed on attempted distillation, were isolated by distilling the solvent. Yields ranged from 70–95%.

The following compounds were made by the methods illustrated above:

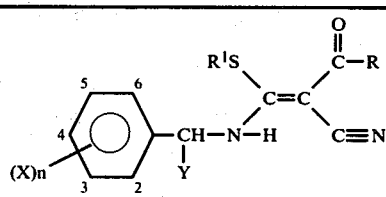

| No. | (X)n | Y | R | R¹ | Physical Prop. m.p. or b.p. (°C.) |
|---|---|---|---|---|---|
| 26 | 4-F | —CH₃ | —NH₂ | —CH₃ | 110–111 |
| 27 | 4-Cl | —CH₃ | —NH₂ | —C₂H₅ | 146–148 |
| 28 | 2,4-dichloro | —H | —NH₂ | —CH₃ | 137–138 |
| 29 | 3,4-dichloro | —CH₃ | —NH₂ | —CH₃ | 119–120 |
| 30 | 4-CH₃ | —CH₃ | —NH₂ | —CH₃ | 146–147 |
| 31 | 3-CH₃ | —H | —NH₂ | —CH₃ | 106–108 |
| 32 | 3-F | —H | —NH₂ | —CH₃ | 101–102 |
| 33 | 4-Br | —CH₃ | —NH₂ | —CH₃ | 133–135 |
| 34 | n=o | —C₂H₅ | —NH₂ | —CH₃ | 116–117 |
| 35 | 3-Br | —CH₃ | —NH₂ | —CH₃ | 168–170 |
| 36 | 4-Br | —C₂H₅ | —NH₂ | —CH₃ | Oil |
| 37 | 3-F | —CH₃ | —NH₂ | —CH₃ | 102–103 |
| 38 | 4-Cl | —C₂H₅ | —NH₂ | —CH₃ | 103–108 |
| 39 | 4-F | —C₂H₅ | —NH₂ | —CH₃ | 135 |
| 40 | 4-CH₃ | —CH₃ | —OCH₃ | —CH₃ | Oil |
| 41 | 3,4-dichloro | —CH₃ | —OCH₃ | —CH₃ | 92–94 |
| 42 | 3-F | H | —OCH₃ | —CH₃ | 79–80 |
| 43 | 3-CH₃ | H | —OCH₃ | —CH₃ | 92–93 |
| 44 | 4-Br | —CH₃ | —OCH₃ | —CH₃ | 90–93 |
| 45 | 3-F | —CH₃ | —OCH₃ | —CH₃ | 72–73 |
| 46 | 3-Br | —CH₃ | —OCH₃ | —CH₃ | 95–96 |
| 47 | n=o | —CH₃ | —OCH₃ | —CH₃ | Oil |
| 48 | n=o | —C₂H₅ | —OCH₃ | —CH₃ | Oil |
| 49 | 4-Cl | —C₂H₅ | —OCH₃ | —CH₃ | Oil |
| 50 | 4-Br | —C₂H₅ | —OCH₃ | —CH₃ | Oil |
| 52 | n=o | —CH₂CH₂CH₃ | —OCH₃ | —CH₃ | 55–60 |
| 53 | 4-Cl | —CH₃ | —OCH₃ | —CH₃ | |
| 54 | 3-CH₃ | —CH₃ | —OCH₃ | —CH₃ | 88–90 |
| 55 | n=o | —CH₃ | —OC₂H₅ | —CH₃ | Oil |
| 56 | 4-Cl | —CH₃ | —OC₂H₅ | —CH₃ | Oil |
| 57 | 4-F | —CH₃ | —OC₂H₅ | —CH₃ | Oil |
| 58 | 3,4-dichloro | —CH₃ | —OC₂H₅ | —CH₃ | Oil |
| 59 | 3-F | —CH₃ | —OC₂H₅ | —CH₃ | Oil |
| 60 | 3-Br | —CH₃ | —OC₂H₅ | —CH₃ | 68–70 |
| 61 | 4-CH₃ | —CH₃ | —OC₂H₅ | —CH₃ | Oil |
| 62 | 4-Cl | —C₂H₅ | —OC₂H₅ | —CH₃ | Oil |
| 63 | 4-F | —C₂H₅ | —OC₂H₅ | —CH₃ | Oil |
| 64 | 4-Br | —C₂H₅ | —OC₂H₅ | —CH₃ | Oil |
| 65 | n=o | L-CH₃ | —OC₂H₅ | —CH₃ | Oil |
| 66 | 4-Cl | H | —OC₂H₅ | —CH₃ | Oil |
| 67 | n=o | H | —OC₂H₅ | —CH₃ | Oil |
| 68 | 3-Cl | H | —OC₂H₅ | —CH₃ | 91–93 |
| 69 | 3-F | H | —OC₂H₅ | —CH₃ | 58–59 |
| 70 | 3,4-dichloro | H | —OC₂H₅ | —CH₃ | 85–88 |
| 71 | 3-NO₂ | H | —OC₂H₅ | —CH₃ | 99–101 |

-continued

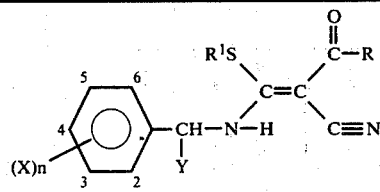

| No. | (X)n | Y | R | R¹ | Physical Prop. m.p. or b.p. (°C.) |
|---|---|---|---|---|---|
| 72 | 4-Br | —CH₃ | —OC₂H₅ | —CH₃ | 93–95 |
| 73 | 3-CH₃ | —CH₃ | —OC₂H₅ | —CH₃ | Oil |
| 74 | 4-F | H | —OCH₂CH=CH₂ | —CH₃ | 41–43 |
| 75 | 3,4-dichloro | H | —OCH₂CH=CH₂ | —CH₃ | Oil |
| 76 | 4-OCH₃ | H | —OCH₂CH=CH₂ | —CH₃ | Oil |
| 77 | 3-Cl | H | —OCH₂CH=CH₂ | —CH₃ | Oil |
| 78 | 4-Br | —CH₃ | —OCH₂CH=CH₂ | —CH₃ | Oil |
| 79 | 4-CH₃ | —CH₃ | —OCH₂CH=CH₂ | —CH₃ | Oil |
| 80 | 4-F | —CH₃ | —OCH₂CH=CH₂ | —CH₃ | Oil |
| 81 | 4-F | —C₂H₅ | —OCH₂CH=CH₂ | —CH₃ | Oil |
| 82 | 4-Cl | —C₂H₅ | —OCH₂CH=CH₂ | —CH₃ | Oil |
| 83 | n=o | —CH(CH₃)₂ | —OCH₂CH=CH₂ | —CH₃ | Oil |
| 84 | 3,4-chloro | H | —O(CH₂)₃CH₃ | —CH₃ | Oil |

Combating Unwanted Vegetation

The novel herbicides may be used selectively to combat unwanted vegetation, both post- and pre-emergently at application rates of 5 lb. per acre or less. Higher application rates may be used pre-emergently if a prolonged effect is desired. However, the high activity of the compounds makes it necessary to apply the compounds in combination with an inert carrier or diluent, preferably water.

So as to obtain a uniform dispersion in water, a surface active agent is also required. The dispersible concentrated formulations may be either in the form of liquid solutions or dispersions, or wettable powders. For pre-emergent use, the herbicides may also be applied in the form of dry granules, which may be made from solutions of the compounds and inert solids, such as clay, according to customary practice. There are described below illustrative procedures for herbicidal use of the compounds under controlled conditions in the greenhouse so as to obtain data on phytotoxic activity and selectivity.

(1) Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The 24 species of plants on which each compound was tested were planted in disposable plastic pots in a greenhouse. Ten to eighteen days after emergence of the plants, three pots of each species were sprayed at each rate with an aqueous dispersion of the active compound prepared as described above, at rates of both 1 lb. and 3 lb. of active compound per acre and at a spray volume of 60 gallons per acre. Approximately one week after the spray application the plants were observed and results were rated according to the following schedule:

DEGREE OF EFFECT

0 = no effect
1 = slight effect
2 = moderate effect
3 = severe effect
4 = maximum effect (all plants died)

The same rating schedule was employed to judge pre-emergent results obtained according to the procedure below.

(2) Pre-Emergent Use

A solution of each active compound was prepared by dissolving 290 mg of the compound to be tested in 200 ml of acetone. Disposable paper trays about 2½ inches deep were filled with soil and sprayed with the acetone solution at rates of 3 lb. and 1 lb. of active chemical per acre of sprayed area, were seeded with 24 species of plant seeds and where then covered with about ¼ inch of soil. Twenty-one days after seeding and treatment the plantings were examined and herbicidal effect was rated according to the above schedule.

Results are tabulated below.

| Compound No. Mode of Application Species | Appl'n. Rate (lb/A) | 26 Pre | 26 Post | 27 Pre | 27 Post | 28 Pre | 28 Post | 29 Pre | 29 Post | 30 Pre | 30 Post | 31 Pre | 31 Post |
|---|---|---|---|---|---|---|---|---|---|---|---|---|---|
| Cocklebur | 3 | 0 | | 0 | 4 | 2 | | 4 | | — | 2 | 4 | |
| (Xanthium pensylvanicum) | 1 | | 4 | | 3 | 1 | | 2 | | — | 0 | 1 | |
| Lambsquarters | 3 | 4 | | 4 | 4 | 4 | | 4 | 4 | 4 | 4 | 4 | |
| (Chenopodium album) | 1 | | 4 | | 4 | 4 | | 4 | 4 | 4 | 4 | 4 | |
| Morning Glory | 3 | 0 | | 0 | 4 | 3 | | 0 | 4 | 0 | 4 | 4 | |
| (Ipomea purpurea) | 1 | | 4 | | 4 | — | | 0 | 3 | 0 | 2 | 1 | |
| Pigweed | 3 | 3 | | 3 | 4 | 4 | | 4 | 4 | 4 | 4 | 4 | |
| (Amaranthus retroflexus) | 1 | | 4 | | 4 | 1 | | 4 | 4 | 4 | 3 | 4 | |
| Wild buckwheat | 3 | 2 | | 3 | 4 | 2 | | 4 | 4 | 3 | 4 | 4 | |

-continued
Results of Pre- and Postemergent Use of Herbicides

| Species | Appl'n Rate (lb/A) | Pre | Post | Pre | Post | Pre | Post | Pre | Post | Pre | Post | Pre | Post |
|---|---|---|---|---|---|---|---|---|---|---|---|---|---|
| (Polygonum convolvulus) | 1 | | 4 | | 4 | 1 | 2 | 3 | 0 | 1 | | 1 | 1 |
| Wild mustard | 3 | 4 | | 4 | 4 | 4 | 4 | 4 | 4 | 4 | | 4 | 4 |
| (Brassica kaber) | 1 | | 4 | | 4 | 4 | 4 | 4 | 4 | 4 | | 4 | 4 |
| Barnyard grass | 3 | 0 | | 0 | 1 | 0 | 0 | 4 | 1 | 1 | | 1 | 2 |
| (Echinochloa crusgalli) | 1 | | 0 | | 0 | 0 | 0 | 1 | 0 | 1 | | 1 | 0 |
| Crabgrass | 3 | 0 | | 0 | 1 | 1 | 1 | 1 | 1 | 2 | | 2 | 1 |
| (Digitaria sanguinalis) | 1 | | 0 | | 0 | 0 | 0 | 0 | 0 | 0 | | 0 | 0 |
| Downey brome | 3 | 0 | | 0 | 1 | 0 | | 1 | 0 | 1 | | 1 | 0 |
| (Bromus tectorum) | 1 | | 0 | | 0 | 0 | 0 | 0 | 0 | 0 | | 0 | 0 |
| Giant foxtail | 3 | 0 | | 0 | 1 | 1 | 1 | 2 | 1 | 4 | | 4 | 1 |
| (Setaria faberii) | 1 | | 1 | | 0 | 0 | 0 | 1 | 0 | 1 | | 1 | 0 |
| Green foxtail | 3 | 0 | | 0 | 1 | 1 | 2 | 4 | 2 | 4 | | 4 | 4 |
| (Setaria viridis) | 1 | | 1 | | 0 | 0 | 1 | 4 | 1 | 3 | | 3 | 0 |
| Nutsedge | 3 | 0 | | 0 | 1 | 0 | 0 | 0 | 0 | 0 | | 0 | 0 |
| (Cyperus esculentus) | 1 | | 0 | | 0 | 0 | 0 | 0 | 0 | 0 | | 0 | 0 |
| Shattercane | 3 | 0 | | 0 | 0 | 0 | 0 | 1 | 0 | 1 | | 1 | 2 |
| (Shorghum bicolor) | 1 | | 0 | | 0 | 0 | 0 | 1 | 0 | 0 | | 0 | 0 |
| Wild oats | 3 | 0 | | 0 | 1 | 0 | 0 | 2 | 0 | 1 | | 1 | 1 |
| (Avena fatua) | 1 | | 1 | | 0 | 0 | 0 | 1 | 0 | 0 | | 0 | 0 |
| Alfalfa | 1 | | 4 | | 4 | 2 | 4 | 4 | 4 | 4 | | 4 | — |
| Cotton | 3 | 0 | | 0 | 4 | 2 | 0 | 4 | 1 | 4 | | 4 | 3 |
| (Gossypium herbaceum) | 1 | | 3 | | 2 | 1 | 0 | 3 | — | 0 | | 0 | 2 |
| Peanuts | 1 | | 1 | | 1 | 0 | 0 | 0 | 0 | 0 | | 0 | 0 |
| Soybeans | 3 | 1 | | 1 | 4 | 3 | 0 | 4 | 0 | 3 | | 3 | 3 |
| (Soja max) | 1 | | 4 | | 4 | 1 | 0 | 4 | 0 | 1 | | 1 | 1 |
| Sugar beets | 3 | 4 | | 1 | 4 | 4 | 4 | 4 | 4 | 4 | | 4 | 4 |
| (Beta vulgaris) | 1 | | 4 | | 4 | 4 | 1 | 4 | 4 | 3 | | 3 | 4 |
| Tomato | 3 | 1 | | 1 | 4 | 4 | 1 | 4 | 0 | 4 | | 4 | 4 |
| (Lycopersicum esculentum) | 1 | | 4 | | 4 | 2 | 0 | 3 | 0 | 1 | | 1 | 2 |
| Corn | 3 | 0 | | 0 | 0 | 0 | 0 | 1 | 0 | 1 | | 1 | 1 |
| (Zea mays) | 1 | | 0 | | 0 | 0 | 0 | 0 | 0 | 0 | | 0 | 0 |
| Grain sorghum | 3 | 0 | | 0 | 0 | 1 | 0 | 1 | 0 | 1 | | 1 | 2 |
| (Sorghum vulgare) | 1 | | 0 | | 0 | 0 | 0 | 1 | 0 | 0 | | 0 | 0 |
| Rice | 1 | | 3 | | 0 | 0 | 0 | 1 | 0 | 0 | | 0 | 0 |
| (Oryza sativa) | 1 | | 3 | | 0 | 0 | 0 | 1 | 0 | 0 | | 0 | 0 |
| Wheat | 3 | 0 | | 0 | 2 | 0 | 0 | 3 | 0 | 1 | | 1 | 3 |
| (Triticum aestivum) | 1 | | 2 | | 0 | 0 | 0 | 2 | 0 | 0 | | 0 | 0 |

| Compound No. | | 32 | | 33 | | 34 | 35 | 36 | | 37 | | | |
|---|---|---|---|---|---|---|---|---|---|---|---|---|---|
| Species | Appl'n Rate (lb/A) | Pre | Post | Pre | Post | Pre | Post | Pre | Post | Pre | Post | Pre | Post |
| Cocklebur | 3 | — | — | 0 | 4 | 0 | 2 | 4 | | 0 | 4 | 1 | 4 |
| (Xanthium pensylvanicum) | 1 | — | — | 0 | 3 | 0 | 1 | 1 | | | 3 | 0 | 3 |
| Lambsquarters | 3 | 4 | 4 | 4 | 4 | 2 | 4 | 4 | | 4 | 4 | 4 | 4 |
| (Chenopodium album) | 1 | 4 | 4 | 4 | 4 | 1 | 4 | 4 | | | 3 | 4 | 4 |
| Morning glory | 3 | 0 | 4 | 0 | 4 | 0 | 4 | 3 | | 1 | 3 | 1 | 4 |
| (Ipomea purpurea) | 1 | 0 | 4 | 0 | 3 | 0 | 1 | 2 | | | 2 | 0 | 2 |
| Pigweed | 3 | 4 | 4 | 4 | 4 | 0 | 1 | 3 | | 3 | 4 | 4 | 4 |
| (Amaranthus retroflexus) | 1 | 4 | 4 | 4 | 3 | 0 | 1 | 3 | | | 1 | 4 | 1 |
| Wild buckwheat | 3 | 4 | 4 | 1 | 4 | 2 | 3 | 4 | | 2 | 4 | 4 | 4 |
| (Polygonum convolvulus) | 1 | 3 | 4 | 0 | 4 | 1 | 1 | 4 | | | 4 | 1 | 3 |
| Wild mustard | 3 | 4 | 4 | 4 | 4 | 4 | 4 | 4 | | 4 | 4 | 4 | 4 |
| (Brassica kaber) | 1 | 4 | 4 | 1 | 4 | 1 | 3 | 3 | | | 3 | 4 | 4 |
| Barnyard grass | 3 | 0 | 3 | 0 | 1 | 0 | 1 | 1 | | 0 | 1 | 3 | 3 |
| (Echinochloa crusgalli) | 1 | 0 | 3 | 0 | 0 | 0 | 0 | 0 | | | 1 | 1 | 0 |
| Crabgrass | 3 | 0 | 4 | 0 | 3 | 1 | 1 | 0 | | 0 | 1 | 4 | 3 |
| (Digitaria sanguinalis) | 1 | 0 | 2 | 0 | 0 | 0 | 0 | 0 | | | 0 | 0 | 0 |
| Downey brome | 3 | 0 | — | 0 | 2 | 0 | 0 | 0 | | 0 | 2 | 1 | 3 |
| (Bromus tectorum) | 1 | 0 | 1 | 0 | 0 | 0 | 0 | 0 | | | 0 | 0 | 0 |
| Giant foxtail | 3 | 0 | 4 | 0 | 3 | 1 | 1 | 0 | | 0 | 2 | 3 | 4 |
| (Setaria faberii) | 1 | 0 | 2 | 0 | 1 | 0 | 0 | 0 | | | 0 | 0 | 0 |
| Green foxtail | 3 | 1 | 4 | 0 | 4 | 0 | 2 | 4 | | 0 | 4 | 4 | 4 |
| (Setaria viridis) | 1 | 0 | 4 | 0 | 1 | 0 | 0 | 1 | | | 2 | 0 | 1 |
| Nutsedge | 3 | 0 | 0 | 0 | 0 | 0 | 0 | 0 | | 0 | 0 | 0 | 0 |
| (Cyperus esculentus) | 1 | 0 | 0 | 0 | 0 | 0 | 0 | 0 | | | 0 | 0 | 0 |
| Shattercane | 3 | 0 | 4 | 0 | 1 | 0 | 0 | 0 | | 0 | 0 | 1 | 1 |
| (Sorghum bicolor) | 1 | 0 | 4 | 0 | 0 | 0 | 0 | 0 | | | 0 | 0 | 0 |
| Wild oats | 3 | 0 | 3 | 0 | 2 | 0 | 1 | 1 | | 0 | 2 | 0 | 3 |
| (Avena fatua) | 1 | 0 | 2 | 0 | 1 | 0 | 1 | 0 | | | 1 | 0 | 2 |
| Alfalfa | 3 | 1 | 4 | 2 | 4 | 2 | 3 | 4 | | 1 | 4 | 1 | 3 |
| (Medicago sativa) | 1 | — | 4 | 0 | 4 | 0 | 2 | 2 | | | 1 | 0 | 1 |
| Cotton | 3 | 0 | 4 | 0 | 3 | 1 | 2 | 2 | | 0 | 3 | 1 | 4 |
| (Gossypium herbaceum) | 1 | 0 | 4 | 0 | 3 | 0 | 1 | 0 | | | 1 | 0 | 3 |
| Peanuts | 3 | 0 | 1 | 0 | 1 | 0 | 1 | 1 | | 0 | 1 | 0 | 1 |
| (Arachis hypogaea) | 1 | 0 | 0 | 0 | 0 | 0 | 0 | 0 | | | 0 | 0 | 1 |
| Soybeans | 3 | 0 | 4 | 0 | 4 | 0 | 3 | 3 | | 0 | 4 | 2 | 4 |
| (Soja max) | | | | | | | | | | | | | |
| (Beta vulgaris) | 3 | 1 | 4 | 3 | 4 | 3 | 3 | 4 | | 2 | 4 | 4 | 4 |
| | 1 | 0 | 4 | 1 | 4 | 0 | 2 | 4 | | | 3 | 1 | 4 |
| Tomato | 3 | 0 | 4 | 0 | 4 | 1 | 3 | 4 | | 1 | 3 | 4 | 4 |
| (Lycopersicum esculentum) | 1 | 0 | 3 | 0 | 0 | 1 | 3 | | | | 1 | 2 | 3 |

-continued

Results of Pre- and Postemergent Use of Herbicides

| Species | | | | | | | | | | | | |
|---|---|---|---|---|---|---|---|---|---|---|---|---|
| Corn | 3 | 0 | 2 | 0 | 0 | 0 | 1 | 0 | 0 | 0 | 1 | 1 |
| (Zea mays) | 1 | 0 | 1 | 0 | 0 | 0 | 0 | 0 | | 0 | 0 | 0 |
| Grain sorghum | 3 | 0 | 4 | 0 | 1 | 0 | 0 | 0 | 0 | 0 | 1 | 2 |
| (Sorghum vulgare) | 1 | 0 | 3 | 0 | 0 | 0 | 0 | | 0 | 0 | 0 | |
| Rice | 3 | 0 | 3 | 1 | 3 | 0 | 0 | 1 | 0 | 1 | 1 | 3 |
| (Oryza sativa) | 1 | 0 | 2 | 0 | 1 | 0 | 0 | 0 | | 0 | 0 | 1 |
| Wheat | 3 | 0 | 3 | 0 | 2 | 0 | 1 | 1 | 0 | 2 | 0 | 2 |
| (Triticum aestivum) | 1 | 0 | 3 | 0 | 1 | 0 | 1 | 0 | | 1 | 0 | 2 |

| Compound No. Mode of Application Species | Appl'n. Rate (lb/A) | 38 PrePost | | 39 PrePost | | 40 PrePost | | 41 PrePost | | 42 PrePost | | 43 PrePost |
|---|---|---|---|---|---|---|---|---|---|---|---|---|
| Cocklebur | 3 | 0 | 4 | 0 | 4 | 0 | 4 | — | 4 | — | 4 | 4 |
| (Xanthium pensylvanicum) | 1 | 0 | 4 | 0 | | 4 | — | — | — | — | 4 | |
| Lambsquarters | 3 | 4 | 4 | 4 | 4 | 4 | 4 | 4 | 4 | 4 | 4 | 4 |
| (Chenopodium album) | 1 | 4 | 4 | 4 | 4 | | 4 | 2 | 4 | 4 | 4 | 4 |
| Morning Glory | 3 | 0 | 4 | 0 | 4 | 0 | 4 | 0 | 4 | 0 | 4 | 4 |
| (Ipomea purpurea) | 1 | 0 | 4 | 0 | 3 | | 4 | 0 | 4 | 0 | 4 | 4 |
| Pigweed | 3 | 4 | 4 | 4 | 4 | 4 | 4 | 4 | 4 | 4 | 4 | 4 |
| (Amaranthus retroflexus) | 1 | 3 | 3 | 4 | 4 | | 4 | 1 | 4 | 4 | 4 | 4 |
| Wild buckwheat | 3 | 2 | 4 | 4 | 4 | 0 | 4 | 0 | 4 | 1 | 4 | 4 |
| (Polygonum convolvulus) | 1 | 1 | 4 | 3 | 4 | | 4 | 0 | 4 | 0 | 4 | 4 |
| Wild mustard | 3 | 4 | 4 | 4 | 4 | 0 | 4 | 4 | 4 | 4 | 4 | 4 |
| (Brassica kaber) | 1 | 1 | 4 | 0 | 4 | | 4 | 0 | 4 | 4 | 4 | 4 |
| Barnyard grass | 3 | 1 | 3 | 2 | 3 | 0 | 4 | 1 | 4 | 2 | 4 | 4 |
| (Echinochloa crusgalli) | 1 | 0 | 2 | 0 | 3 | | 4 | 0 | 3 | 1 | 4 | 4 |
| Crabgrass | 3 | 1 | 3 | 3 | 4 | 2 | 4 | 1 | 4 | 4 | 4 | 4 |
| (Digitaria sanguinalis) | 1 | 0 | 1 | 1 | 1 | | 4 | 0 | 4 | 3 | 4 | 4 |
| Downey brome | 3 | 0 | 3 | 1 | 3 | 1 | 4 | 0 | 3 | 0 | 4 | 4 |
| (Bromus tectorum) | 1 | 0 | 1 | 0 | 1 | | 2 | 0 | — | 0 | 1 | 1 |
| Giant foxtail | 3 | 2 | 3 | 3 | 4 | 1 | 4 | 1 | 4 | 2 | 4 | 4 |
| (Setaria faberii) | 1 | 0 | 2 | 0 | 2 | | 4 | 0 | 4 | 1 | 4 | 4 |
| Green foxtail | 3 | 2 | 4 | 3 | 4 | 1 | 4 | 2 | 4 | 4 | 4 | 4 |
| (Setaria viridis) | 1 | 0 | 4 | 1 | 4 | | 4 | 2 | 4 | 2 | 4 | 4 |
| Nutsedge | 3 | 0 | 3 | 0 | 1 | 0 | 0 | 0 | 1 | 0 | 1 | 1 |
| (Cyperus esculentus) | 1 | 0 | 0 | 0 | 0 | | 0 | 0 | 0 | 0 | 0 | 0 |
| Shattercane | 3 | 0 | 2 | 0 | 2 | 0 | 4 | 0 | 4 | 0 | 4 | 3 |
| (Sorghum bicolor) | 1 | 0 | 1 | 0 | −1 | | 3 | 0 | 4 | 0 | 4 | 3 |
| Wild oats | 3 | 0 | 4 | 0 | 4 | 0 | 4 | 0 | 4 | 0 | 4 | 3 |
| (Avena fatua) | 1 | 0 | 3 | 0 | 3 | | 3 | 0 | 3 | 0 | 3 | 3 |
| Alfalfa | 3 | 1 | 4 | 2 | 4 | 0 | 4 | 4 | 4 | 4 | 4 | 4 |
| (Medicago sativa) | 1 | 0 | 4 | 0 | 3 | | 4 | 2 | 4 | 4 | 4 | 4 |
| Cotton | 3 | 0 | 4 | 0 | 4 | 0 | 4 | 0 | 4 | 1 | 4 | 4 |
| (Gossypium herbaceum) | 1 | 0 | 4 | 0 | 4 | | 3 | 0 | 4 | 0 | 3 | 3 |
| Peanuts | 3 | 0 | 2 | 0 | 2 | 0 | 0 | 0 | 2 | 0 | 1 | — |
| (Arachis hypogaea) | 1 | 0 | 1 | 0 | 1 | | 0 | 0 | — | 0 | 0 | 1 |
| Soybeans | 3 | 0 | 4 | 0 | 4 | 0 | 4 | 0 | 4 | 4 | 4 | 4 |
| (Soja max) | 1 | 0 | 4 | 0 | 4 | | 1 | 0 | 4 | 1 | 4 | 4 |
| Sugar beets | 3 | 2 | 4 | 4 | 4 | 0 | 4 | 1 | 4 | 2 | 4 | 4 |
| (Beta vulgaris) | 1 | 1 | 4 | 2 | 4 | | 4 | 0 | 4 | 0 | 4 | 4 |
| Tomato | 3 | 1 | 4 | 3 | 4 | 0 | 4 | 0 | 4 | 1 | 4 | 4 |
| (Lycopersicum esculentum) | 1 | 0 | 3 | 1 | 4 | | 4 | 0 | 4 | 0 | 3 | 4 |
| Corn | 3 | 0 | 3 | 0 | 3 | 0 | 4 | 0 | 4 | 0 | 4 | 4 |
| (Zea mays) | 1 | 0 | 2 | 0 | 2 | | 2 | 0 | 2 | 0 | 3 | 2 |
| Grain sorghum | 3 | 0 | 2 | 0 | 3 | 0 | 4 | 0 | 4 | 0 | 4 | 3 |
| (Sorghum vulgare) | 1 | 0 | 1 | 0 | 1 | | 4 | 0 | 4 | 0 | 4 | 3 |
| Rice | 3 | 0 | 3 | 0 | 3 | 0 | 4 | 0 | 4 | 0 | 4 | 3 |
| (Oryza sativa) | 1 | 0 | 2 | 0 | 1 | | 2 | 0 | 3 | — | 2 | 2 |
| Wheat | 3 | 0 | 4 | 0 | 4 | 0 | 4 | 0 | 4 | 0 | 4 | 2 |
| (Tricicum aestivum) | 1 | 0 | 3 | 0 | 3 | | 3 | 0 | 3 | 0 | 3 | 2 |

| Compound No. Mode of Application Species | Appl'n. Rate (lb/A) | 44 PrePost | | 45 PrePost | | 46 PrePost | | 47 PrePost | | 48 PrePost | | 49 PrePost |
|---|---|---|---|---|---|---|---|---|---|---|---|---|
| Cocklebur | 3 | 1 | 4 | 0 | 4 | 4 | 0 | 4 | | 2 | 0 | 4 |
| (Xanthium pennsylvanicum) | 1 | 0 | 4 | 0 | 3 | 3 | 0 | 2 | | 1 | 0 | 4 |
| Lambsquarters | 3 | 4 | 4 | 4 | 4 | 4 | 4 | 4 | | 4 | 4 | 4 |
| (Chenopodium album) | 1 | 4 | 4 | 2 | 4 | 3 | 2 | 4 | | 2 | 3 | 4 |
| Morning glory | 3 | 1 | 4 | 0 | 4 | 4 | 0 | 4 | | 4 | 0 | 4 |
| (Iponmea purpurea) | 1 | 0 | 4 | 0 | 3 | 2 | 0 | 2 | | 1 | 0 | 4 |
| Pigweed | 3 | 4 | 3 | 2 | 4 | 3 | 1 | 1 | | 2 | 2 | 4 |
| (Amaranthus retroflexus) | 1 | 0 | 3 | 0 | 2 | 0 | 0 | 1 | | 0 | 0 | 4 |
| Wild buckwheat | 3 | 1 | 4 | 3 | 4 | 4 | 1 | 4 | | 4 | 3 | 4 |
| (Polygonum convolvulus) | 1 | 0 | 4 | 0 | 4 | 4 | 1 | 4 | | 4 | 1 | 4 |
| Wild mustard | 3 | 4 | 4 | 4 | 4 | 4 | 4 | 4 | | 4 | 4 | 4 |
| (Brassica kaber) | 1 | 4 | 4 | 1 | 4 | 4 | 2 | 4 | | 4 | 0 | 4 |
| Barnyard grass | 2 | 0 | 2 | 3 | 3 | 2 | 3 | 3 | | 2 | 2 | 3 |
| (Echinochloa crusgalli) | 1 | 0 | 1 | 1 | 3 | 0 | 2 | 2 | | 1 | 2 | 1 |
| Crabgrass | 3 | 1 | 1 | 4 | 1 | 2 | 2 | 1 | | 1 | 3 | 2 |

-continued
Results of Pre- and Postemergent Use of Herbicides

| Species | Rate (lb/A) | | | | | | | | | | | | |
|---|---|---|---|---|---|---|---|---|---|---|---|---|---|
| (Digitaria sanguinalis) | 1 | 1 | 1 | 0 | 1 | 1 | 1 | 1 | 0 | 1 | 0 | | |
| Downey brome | 3 | 1 | 2 | 1 | 3 | 2 | 0 | 0 | 0 | 1 | 3 | | |
| (Bromus tectorum) | 1 | 0 | 2 | 0 | 0 | 0 | 0 | 0 | 0 | 0 | 0 | | |
| Giant foxtail | 3 | 1 | 3 | 2 | 4 | 2 | 1 | 1 | 1 | 4 | 3 | | |
| (Setaria faberii) | 1 | 0 | 3 | 0 | 1 | 1 | 1 | 1 | 1 | 1 | 0 | | |
| Green foxtail | 3 | 2 | 4 | 4 | 4 | 3 | 4 | 4 | 2 | 4 | 4 | | |
| (Setaria viridis) | 1 | 0 | 4 | 1 | 3 | 2 | 3 | 2 | 2 | 3 | 4 | | |
| Nutsedge | 3 | 0 | 0 | 0 | 1 | 0 | 0 | 0 | 0 | 0 | 0 | | |
| (Cyperus esculentus) | 1 | 0 | 0 | 0 | 0 | 0 | 0 | 0 | 0 | 0 | 0 | | |
| Shattercane | 3 | 0 | 2 | 0 | 1 | 0 | 0 | 0 | 0 | 0 | 1 | | |
| (Sorghum bicolor) | 1 | 0 | 1 | 0 | 0 | 0 | 0 | 0 | 0 | 0 | 0 | | |
| Wild oats | 3 | 1 | 4 | 0 | 3 | 3 | 0 | 2 | 3 | 0 | 4 | | |
| (Avena fatua) | 1 | 0 | 2 | 0 | 1 | 2 | 0 | 1 | 1 | 0 | 4 | | |
| Alfalfa | 3 | 1 | 4 | 3 | 4 | 4 | 3 | 4 | 4 | 3 | 4 | | |
| (Medicago sativa) | 1 | — | 4 | 0 | 4 | 3 | 0 | 3 | 4 | 2 | 4 | | |
| Cotton | 3 | 0 | 4 | 0 | 4 | 4 | 0 | 4 | 2 | 0 | 4 | | |
| (Gossypium herbaceum) | 1 | 0 | 4 | 0 | 4 | 3 | 0 | 2 | 1 | 0 | 4 | | |
| Peanuts | 3 | 0 | 2 | 0 | 1 | 1 | 0 | 1 | 1 | 0 | 1 | | |
| (Arachis hypogaea) | 1 | 0 | 1 | 0 | 1 | 0 | 0 | 1 | 1 | 0 | 1 | | |
| Soybeans | 3 | 1 | 4 | 0 | 4 | 4 | 0 | 4 | 3 | 0 | 4 | | |
| (Soja max) | 1 | 0 | 4 | 0 | 4 | 4 | 0 | 2 | 3 | 0 | 4 | | |
| Sugar beets | 3 | 1 | 4 | 4 | 4 | 4 | 3 | 4 | 4 | 4 | 4 | | |
| (Beta vulgaris) | 1 | 0 | 4 | 0 | 4 | 4 | 3 | 4 | 4 | 1 | 4 | | |
| Tomato | 3 | 0 | 4 | 2 | 4 | 4 | 1 | 4 | 2 | 0 | 3 | | |
| (Lucopersicum esculentum) | 1 | 0 | 4 | 0 | 3 | 3 | 0 | 2 | 2 | 0 | 3 | | |
| Corn | 3 | 0 | 1 | 0 | 1 | 0 | 2 | 1 | 0 | 0 | 1 | | |
| (Zea mays) | 1 | 0 | 0 | 0 | 0 | 0 | 0 | 0 | 0 | 0 | 0 | | |
| Grain sorghum | 3 | 0 | 2 | 0 | 1 | 0 | 0 | 0 | 0 | 0 | 2 | | |
| (Sorghum vulgare) | 1 | 0 | 1 | 0 | 0 | 0 | 0 | 0 | 0 | 0 | 0 | | |
| Rice | 3 | 1 | 4 | | | 3 | — | — | — | — | — | | |
| (Oryza sativa) | 1 | 0 | 2 | | | 1 | 0 | — | — | — | — | | |
| Wheat | 3 | 0 | 3 | 0 | 2 | — | 0 | 1 | 1 | 0 | 2 | | |
| (Triticum aestivum) | 1 | 0 | 3 | 0 | 1 | — | 0 | 1 | 1 | 0 | 1 | | |

| Compound No. | | 50 | | 51 | | 52 | | 53 | | 54 | | 55 | |
|---|---|---|---|---|---|---|---|---|---|---|---|---|---|
| Mode of Application | Appl'n. Rate | Pre | Post | Pre | Post | Pre | Post | Pre | Post | Pre | Post | Pre | Post |
| Species | (lb/A) | | | | | | | | | | | | |
| Cocklebur | 3 | 0 | 4 | 0 | 4 | 4 | | 4 | | 4 | 0 | 4 | |
| (Xanthium pensylvanicum) | 1 | 0 | 4 | 0 | 4 | 0 | | 2 | | 1 | 0 | 0 | |
| Lambsquarters | 3 | 3 | 4 | 4 | 4 | 4 | | 4 | | 4 | 4 | 4 | |
| (Chenopodium album) | 1 | 2 | 4 | 4 | 4 | 4 | | 4 | | 4 | 1 | 2 | |
| Morning glory | 3 | 0 | 4 | 0 | 4 | 1 | | 4 | | 4 | 1 | 2 | |
| (Ipomea purpurea) | 1 | 0 | 3 | 0 | 3 | 0 | | 1 | | 1 | 0 | 1 | |
| Pigweed | 3 | 1 | 4 | 1 | 4 | 3 | | 3 | | 4 | 0 | 2 | |
| (Aramanthus retroflexus) | 1 | 0 | 4 | 0 | 4 | 1 | | 1 | | 2 | 0 | 0 | |
| Wild buckwheat | 3 | 2 | 4 | 4 | 4 | 4 | | 4 | | 4 | 1 | 4 | |
| (Polygonum convolvulus) | 1 | 0 | 4 | 0 | 4 | 4 | | 4 | | 3 | 0 | 4 | |
| Wild mustard | 3 | 4 | 4 | 4 | 4 | 4 | | 4 | | 4 | 3 | 4 | |
| (Brassica kaber) | 1 | 1 | 4 | 0 | 4 | 3 | | 4 | | 4 | 0 | 4 | |
| Barnyard grass | 3 | 1 | 1 | 2 | 4 | 1 | | 1 | | 3 | 1 | 3 | |
| (Echinochloa crusgalli) | 1 | 0 | 1 | 1 | 3 | 0 | | 0 | | 2 | 0 | 1 | |
| Crabgrass | 3 | 1 | 1 | 4 | 3 | 0 | | 0 | | 1 | 3 | 2 | |
| (Digitaria sanguinalis) | 1 | 0 | 1 | 0 | 3 | 0 | | 0 | | 0 | 0 | 0 | |
| Downey brome | 3 | 0 | — | 1 | 4 | 0 | | 0 | | 0 | 1 | 1 | |
| (Bromus tectorum) | 1 | 0 | 1 | 0 | 2 | 0 | | 0 | | 0 | 0 | 0 | |
| Giant foxtail | 3 | 2 | 1 | 3 | 4 | 2 | | 0 | | 1 | 2 | 3 | |
| (Setaria faberii) | 1 | 0 | 1 | 1 | 2 | 0 | | 0 | | 0 | 0 | 0 | |
| Green foxtail | 3 | 3 | 4 | 4 | 4 | 4 | | 1 | | 4 | 2 | 4 | |
| (Setaria viridis) | 1 | 0 | 2 | 2 | 4 | 1 | | 0 | | 2 | 0 | 0 | |
| Nutsedge | 3 | 0 | 1 | 0 | 1 | 0 | | 0 | | 0 | 0 | 0 | |
| (Cyperus esculentus) | 1 | 0 | 0 | 0 | 0 | 0 | | 0 | | 0 | 0 | 0 | |
| Shattercane | 3 | 0 | 1 | 0 | 3 | 1 | | 0 | | 1 | 0 | 1 | |
| (Shorghum bicolor) | 1 | 0 | 0 | 0 | 2 | 0 | | 0 | | 0 | 0 | 0 | |
| Wild oats | 3 | 0 | 4 | 0 | 4 | 2 | | 2 | | 3 | 0 | 2 | |
| (Avena fatua) | 1 | 0 | 2 | 0 | 4 | 0 | | 1 | | 0 | 0 | 1 | |
| Alfalfa | 3 | 4 | 4 | 4 | 4 | 4 | | 4 | | 4 | 1 | 3 | |
| (Medicago sativa) | 1 | 0 | 4 | 2 | 4 | 2 | | 2 | | 4 | 0 | 1 | |
| Cotton | 3 | 0 | 4 | 0 | 4 | 1 | | 1 | | 4 | 1 | 3 | |
| (Gossypium herbaceum) | 1 | 0 | 4 | 0 | 3 | 1 | | 1 | | 3 | 0 | 1 | |
| Peanuts | 3 | 0 | 1 | 0 | 3 | 0 | | 0 | | 3 | 0 | 1 | |
| (Arachis hypogaea) | 1 | 0 | 1 | 0 | 1 | 0 | | 0 | | 0 | 0 | 0 | |
| Soybeans | 3 | 0 | 3 | 0 | 4 | 2 | | 4 | | 4 | 0 | 3 | |
| (Soja max) | 1 | 0 | 3 | 0 | 3 | 1 | | 1 | | 1 | 0 | 2 | |
| Sugar beets | 3 | 1 | 4 | 4 | 4 | 4 | | 4 | | 4 | 1 | 4 | |
| (Beta vulgaris) | 1 | 0 | 4 | 0 | 4 | 2 | | 4 | | 3 | 0 | 2 | |
| Tomato | 3 | 0 | 2 | 1 | 4 | 2 | | 2 | | 4 | 0 | 4 | |
| (Lycopersicum esculentum) | 1 | 0 | 1 | 0 | 3 | 1 | | 1 | | 4 | 0 | 2 | |
| Corn | 3 | 1 | 1 | 1 | 3 | 4 | | 0 | | 1 | 0 | 2 | |
| (Zea mays) | 1 | 0 | 0 | 0 | 1 | 0 | | 0 | | 1 | 0 | 0 | |
| Grain sorghum | 3 | 0 | 1 | 0 | 4 | 1 | | 0 | | 1 | 0 | 1 | |

-continued
Results of Pre- and Postemergent Use of Herbicides

| | | | | | | | | | | | | |
|---|---|---|---|---|---|---|---|---|---|---|---|---|
| Rice | 3 | 0 | — | — | — | 1 | | 0 | | 3 | 0 | 1 |
| (*Oryza sativa*) | 1 | — | — | 0 | — | 0 | | 0 | | 1 | 0 | 0 |
| Wheat | 3 | 0 | 3 | 0 | 3 | 1 | | 2 | | 3 | 0 | 1 |
| (*Tricicum aestivum*) | 1 | 0 | 1 | 0 | 3 | 0 | | 1 | | 0 | 0 | 0 |

| Compound No. | Appl'n. | 56 | | 57 | | 58 | | 59 | | 60 | | 61 | |
| Mode of Application | Rate | | | | | | | | | | | | |
| Species | (lb/A) | Pre | Post | Pre | Post | Pre | Post | Pre | Post | Pre | Post | Pre | Post |
|---|---|---|---|---|---|---|---|---|---|---|---|---|---|
| Cocklebur | 3 | 0 | 4 | 0 | 4 | 0 | 4 | 0 | 4 | 0 | 4 | 0 | 4 |
| (*Xanthium pensylvanicum*) | 1 | 0 | 4 | 0 | 3 | 0 | 4 | 0 | 2 | | 3 | 0 | 3 |
| Lambsquarters | 3 | 4 | 4 | 4 | 4 | 4 | 4 | 4 | 4 | 2 | 4 | 4 | 4 |
| (*Chenopodium album*) | 1 | 4 | 4 | 4 | 4 | 1 | 4 | 3 | 3 | | 2 | 2 | 4 |
| Morning glory | 3 | 0 | 4 | 0 | 3 | 0 | 4 | 0 | 3 | 0 | 4 | 0 | 4 |
| (*Ipomea purpurea*) | 1 | 0 | 3 | 0 | 1 | 0 | 4 | 0 | 1 | | 2 | 0 | 3 |
| Pigweed | 3 | 3 | 2 | 4 | 3 | 4 | 3 | 1 | 1 | 0 | 1 | 1 | 2 |
| (*Amaranthus retroflexus*) | 1 | 2 | 2 | 1 | 2 | 1 | 1 | 1 | 0 | | 0 | 0 | 0 |
| Wild buckwheat | 3 | 2 | 4 | 3 | 4 | 4 | 4 | 3 | 4 | 0 | 4 | 2 | 4 |
| (*Polygonum convolvulus*) | 1 | 1 | 4 | 1 | 4 | 2 | 4 | 1 | 4 | | 4 | 0 | 4 |
| Wild mustard | 3 | 4 | 4 | 4 | 4 | 4 | 4 | 4 | 4 | 0 | 4 | 4 | 4 |
| (*Brassica kaber*) | 1 | 2 | 4 | 1 | 4 | 1 | 4 | 1 | 4 | | 4 | 0 | 4 |
| Barnyard grass | 3 | 2 | 4 | 2 | 4 | 2 | 4 | 3 | 4 | 0 | 3 | 1 | 4 |
| (*Echinochloa crusgalli*) | 1 | 2 | 3 | 1 | 2 | 1 | 1 | 1 | 3 | | 1 | 0 | 3 |
| Crabgrass | 3 | 4 | 2 | 4 | 4 | 4 | 2 | 4 | 4 | 1 | 1 | 4 | 3 |
| (*Digitaria sanguinalis*) | 1 | 1 | 2 | 1 | 2 | 2 | 0 | 1 | 1 | | 1 | 0 | 2 |
| Downey brome | 3 | 0 | 3 | 1 | 3 | 2 | 2 | 1 | 1 | 0 | 1 | 0 | 2 |
| (*Bromus tectorum*) | 1 | 0 | 0 | 0 | 1 | 1 | 0 | 0 | 0 | | 1 | 0 | 1 |
| Giant foxtail | 3 | 4 | 4 | 4 | 4 | 4 | 3 | 4 | 4 | 0 | 2 | 2 | 2 |
| (*Setaria faberii*) | 1 | 2 | 2 | 1 | 3 | 1 | 1 | 1 | 2 | | 1 | 0 | 2 |
| Green foxtail | 3 | 3 | 4 | 4 | 4 | 4 | 4 | 3 | 4 | 0 | 4 | 2 | 4 |
| (*Setaria viridis*) | 1 | 2 | 3 | 1 | 4 | 0 | 3 | 1 | 4 | | 2 | 0 | 4 |
| Nutsedge | 3 | 0 | 1 | 0 | 2 | 0 | 2 | 0 | 1 | 0 | 0 | 0 | 1 |
| (*Cyperus esculentus*) | 1 | 0 | 0 | 0 | 1 | 0 | 0 | 0 | 0 | | 0 | 0 | 0 |
| Shattercane | 3 | 0 | 2 | 0 | 3 | 0 | 2 | 0 | 1 | 0 | 1 | 0 | 2 |
| (*Sorghum bicolor*) | 1 | 0 | 1 | 0 | 1 | 0 | 0 | 0 | 0 | | 0 | 0 | 0 |
| Wild oats | 3 | 0 | 4 | 1 | 3 | 1 | 4 | 1 | 2 | 0 | 3 | 0 | 4 |
| (*Avena fatua*) | 1 | 0 | 2 | 0 | 1 | 0 | 2 | 0 | 0 | | 1 | 0 | 1 |
| Alfalfa | 3 | 4 | 4 | 4 | 4 | 4 | 4 | 3 | 4 | 1 | 3 | 2 | 4 |
| (*Medicago sativa*) | 1 | 3 | 4 | 1 | 4 | 1 | 4 | 0 | 3 | | 3 | 0 | 2 |
| Cotton | 3 | 0 | 4 | 0 | 4 | 1 | 4 | 0 | 4 | 0 | 4 | 0 | 4 |
| (*Gossypium herbaceum*) | 1 | 0 | 4 | 0 | 4 | 0 | 4 | 0 | 1 | | 4 | 0 | 3 |
| Peanuts | 3 | 0 | 2 | 0 | 2 | 0 | 2 | 0 | 1 | 0 | 1 | 0 | 1 |
| (*Arachis hypogaea*) | 1 | 0 | 2 | 0 | 1 | 0 | 2 | 0 | 1 | | 1 | 0 | 1 |
| Soybeans | 3 | 0 | 4 | 0 | 4 | 0 | 4 | 0 | 4 | 0 | 3 | 0 | 3 |
| (*Soja max*) | 1 | 0 | 2 | 0 | 3 | 0 | 3 | 0 | 3 | | 3 | 0 | 3 |
| Sugar beets | 3 | 0 | 4 | 1 | 4 | 3 | 4 | 1 | 4 | 0 | 4 | 0 | 4 |
| (*Beta vulgaris*) | 1 | 0 | 4 | 0 | 3 | 1 | 4 | 0 | 4 | | 4 | 0 | 3 |
| Tomato | 3 | 3 | 4 | 4 | 4 | 4 | 4 | 3 | 4 | 0 | 4 | 2 | 4 |
| (*Lycopersicum esculentum*) | 1 | 3 | 4 | 2 | 4 | 3 | 4 | 3 | 3 | | 4 | 1 | 3 |
| Corn | 3 | 0 | 1 | 1 | 3 | 0 | 2 | 0 | 1 | 0 | 2 | 0 | 2 |
| (*Zea mays*) | 1 | 0 | 1 | 0 | 2 | 0 | 1 | 0 | 0 | | 0 | 0 | 0 |
| Grain sorghum | 3 | 0 | 2 | 0 | 3 | 0 | 2 | 0 | 1 | 0 | 1 | 0 | 2 |
| (*Sorghum vulgare*) | 1 | 0 | 1 | 0 | 1 | 0 | 0 | 0 | 0 | | 0 | 0 | 0 |
| Rice | 3 | 0 | 2 | 0 | 3 | 0 | 1 | 0 | 1 | 0 | 1 | 0 | 2 |
| (*Oryza sativa*) | 1 | 0 | 1 | 0 | 1 | 0 | 1 | 0 | 0 | | 0 | 0 | 0 |
| Wheat | 3 | 1 | 4 | 1 | 4 | 1 | 3 | 1 | 2 | 0 | 3 | 0 | 2 |
| (*Tricium aestivum*) | 1 | 0 | 2 | 0 | 2 | 0 | 2 | 0 | 0 | | 0 | 0 | 0 |

| Compound No. | Appl'n. | 62 | | 63 | | 64 | | 65 | | 66 | | 67 | |
| Mode of Application | Rate | | | | | | | | | | | | |
| Species | (lb/A) | Pre | Post | Pre | Post | Pre | Post | Pre | Post | Pre | Post | Pre | Post |
|---|---|---|---|---|---|---|---|---|---|---|---|---|---|
| Cocklebur | 3 | 0 | 4 | 0 | 4 | 0 | 4 | 0 | 2 | 0 | 4 | 0 | 3 |
| (*Xanthium pensylvanicum*) | 1 | 0 | 4 | 0 | 3 | 0 | 4 | 0 | 0 | 0 | 2 | 0 | 2 |
| Lambsquarters | 3 | 4 | 4 | 4 | 4 | 4 | 4 | 4 | 4 | 4 | 4 | 4 | 4 |
| (*Chenopodium album*) | 1 | 1 | 4 | 1 | 4 | 1 | 4 | 3 | 2 | 3 | 3 | 3 | 4 |
| Morning glory | 3 | 0 | 4 | 0 | 4 | 0 | 4 | 0 | 2 | 0 | 3 | 0 | 2 |
| (*Ipomea purpurea*) | 1 | 0 | 4 | 0 | 2 | 0 | 4 | 0 | 1 | 0 | 1 | 0 | 1 |
| Pigweed | 3 | 3 | 2 | 3 | 4 | 3 | 3 | 3 | 1 | 3 | 3 | 3 | 4 |
| (*Amaranthus retroflexus*) | 1 | 0 | 2 | 0 | 2 | 0 | 1 | 0 | 0 | 0 | 1 | 0 | 2 |
| Wild buckwheat | 3 | 2 | 4 | 1 | 4 | 1 | 4 | 4 | 4 | 4 | 4 | 3 | 4 |
| (*Polygonum convolvulus*) | 1 | 0 | 4 | 0 | 4 | 0 | 4 | 2 | 3 | 2 | 4 | 1 | 4 |
| Wild mustard | 3 | 4 | 4 | 4 | 4 | 4 | 4 | 4 | 4 | 4 | 4 | 4 | 4 |
| (*Brassica kaber*) | 1 | 0 | 4 | 0 | 4 | 3 | 4 | 2 | 4 | 4 | 3 | 2 | 2 |
| Barnyard grass | 3 | 1 | 3 | 3 | 4 | 1 | 2 | 3 | 4 | 0 | 3 | 0 | 3 |
| (*Echinochloa crusgalli*) | 1 | 1 | 1 | 2 | 2 | 1 | 0 | 3 | 1 | 0 | 1 | 0 | 0 |
| Crabgrass | 3 | 4 | 1 | 4 | 3 | 2 | 1 | 4 | 2 | 3 | 1 | 1 | 2 |
| (*Digitaria sanguinalis*) | 1 | 1 | 0 | 2 | 1 | 1 | 0 | 3 | 1 | 0 | 0 | 0 | 0 |
| Downey brome | 3 | 1 | 1 | 1 | 2 | 1 | 1 | 1 | 2 | 0 | 2 | 0 | 2 |
| (*Bromus tectorum*) | 1 | 0 | 0 | 0 | 0 | 0 | 0 | 1 | 0 | 0 | 0 | 0 | |
| Giant foxtail | 3 | 4 | 1 | 3 | 2 | 3 | 2 | 4 | 2 | 1 | 1 | 0 | 0 |
| (*Setaria faberii*) | 1 | 0 | 1 | 0 | 0 | 0 | 0 | 2 | 0 | 0 | 0 | 0 | |

4,201,569

-continued
Results of Pre- and Postemergent Use of Herbicides

| Species | Appl'n Rate (lb/A) | PrePost | PrePost | PrePost | PrePost | PrePost | PrePost |
|---|---|---|---|---|---|---|---|
| Green foxtail (Setaria viridis) | 3 | 3 4 | 3 4 | 2 4 | 4 4 | 0 4 | 0 3 |
|  | 1 | 0 4 | 1 4 | 0 2 | 2 2 | 0 2 | 0 2 |
| Nutsedge (Cyperus esculentus) | 3 | 0 2 | 0 0 | 0 0 | 0 0 | 1 0 | 0 0 |
|  | 1 | 0 1 | 0 0 | 0 0 | 0 0 | 0 0 | 0 |
| Shattercane (Sorghum bicolor) | 3 | 0 2 | 0 3 | 0 1 | 3 1 | 0 2 | 0 2 |
|  | 1 | 0 0 | 0 1 | 0 0 | 1 1 | 0 0 | 0 0 |
| Wild oats (Avena fatua) | 3 | 0 4 | 0 4 | 0 2 | 1 2 | 1 4 | 1 4 |
|  | 1 | 0 3 | 0 3 | 0 1 | 0 1 | 0 2 | 0 2 |
| Alfalfa (Medicago sativa) | 3 | 1 4 | 4 4 | 4 4 | 4 4 | 1 4 | 4 4 |
|  | 1 | 0 4 | 0 4 | 0 4 | 1 1 | 1 4 | 2 3 |
| Cotton (Gossypium herbaceum) | 3 | 0 4 | 0 4 | 0 3 | 0 3 | 0 3 | 0 1 |
|  | 1 | 0 4 | 0 3 | 0 3 | 0 1 | 0 1 | 0 1 |
| Peanuts (Arachis hypogaea) | 3 | 0 1 | 0 1 | 0 1 | 0 1 | 0 1 | 0 1 |
|  | 1 | 0 1 | 0 0 | 0 1 | 0 0 | 0 1 | 0 0 |
| Soybeans (Soja max) | 3 | 0 4 | 0 3 | 0 3 | 0 4 | 0 3 | 0 2 |
|  | 1 | 0 2 | 0 2 | 0 2 | 0 1 | 0 1 | 0 2 |
| Sugar beets (Beta vulgaris) | 3 | 0 4 | 0 4 | 0 4 | 2 4 | 2 4 | 2 4 |
|  | 1 | 0 4 | 0 4 | 0 4 | 0 4 | 2 4 | 0 4 |
| Tomato (Lycopersicum esculentum) | 3 | 1 3 | 0 4 | 1 4 | 3 4 | 1 4 | 1 4 |
|  | 1 | 1 3 | 0 4 | 0 3 | 0 3 | 0 2 | 1 2 |
| Corn (Zea mays) | 3 | 0 1 | 0 2 | 0 1 | 1 2 | 0 1 | 0 1 |
|  | 1 | 0 0 | 0 0 | 0 0 | 0 1 | 0 0 | 0 0 |
| Grain sorghum (Sorghum vulgare) | 3 | 0 2 | 0 3 | 0 1 | 3 2 | 0 2 | 0 1 |
|  | 1 | 0 0 | 0 1 | 0 0 | 1 1 | 0 0 | 0 0 |
| Rice (Oryza sativa) | 3 | 0 1 | 0 2 | 0 1 | 0 2 | 0 0 | 0 2 |
|  | 1 | 0 1 | 0 1 | 0 0 | 0 1 | 0 0 | 0 1 |
| Wheat (Tricium aestivum) | 3 | 0 4 | 0 4 | 0 3 | 1 2 | 0 4 | 0 4 |
|  | 1 | 0 3 | 0 3 | 0 1 | 0 1 | 0 1 | 0 1 |

| Compound No. Mode of Application Species | Appl'n Rate (lb/A) | 68 PrePost | 69 PrePost | 70 PrePost | 71 PrePost | 72 PrePost | 73 PrePost |
|---|---|---|---|---|---|---|---|
| Cocklebur (Xanthium pensylvanicum) | 3 | 4 | 0 3 | 0 4 | 2 | 4 | 4 |
|  | 1 | 2 | 0 1 | 4 | 2 | 4 | 2 |
| Lambsquarters (Chenopodium album) | 3 | 4 | 4 4 | 3 4 | 4 | 4 | 4 |
|  | 1 | 4 | 2 4 | 4 | 4 | 4 | 4 |
| Morning glory (Ipomea purpurea) | 3 | 3 | 0 1 | 0 4 | 1 | 4 | 4 |
|  | 1 | 1 | 0 0 | 4 | 0 | 4 | 3 |
| Pigweed (Amaranthus retroflexus) | 3 | 2 | 3 4 | 2 3 | 3 | 4 | 4 |
|  | 1 | 1 | 0 3 | 3 | 3 | 4 | 4 |
| Wild buckwheat (Polygonum convolvulus) | 3 | 4 | 3 4 | 0 4 | 4 | 4 | 4 |
|  | 1 | 4 | 0 4 | 4 | 3 | 4 | 3 |
| Wild mustard (Brassica kaber) | 3 | 4 | 4 3 | — | 4 | 4 | 4 |
|  | 1 | 4 | 1 2 | 4 | 4 | 4 | 2 |
| Barnyard grass (Echinochloa crusgalli) | 3 | 2 | 0 1 | 1 3 | 0 | 1 | 3 |
|  | 1 | 1 | 0 1 | 1 | 0 | 1 | 3 |
| Crabgrass (Digitaria sanguinalis) | 3 | 1 | 0 4 | 2 1 | 0 | 2 | 3 |
|  | 1 | 1 | 0 1 | 0 | 0 | 1 | 2 |
| Downey brome (Bromus tectorum) | 3 | 2 | 0 3 | 0 1 | 0 | 1 | 3 |
|  | 1 | 0 | 0 0 | 0 | 0 | 0 | 1 |
| Giant foxtail (Setaria faberii) | 3 | 1 | 0 2 | 1 1 | 1 | 2 | 3 |
|  | 1 | 0 | 0 1 | 0 | 0 | 1 | 1 |
| Green foxtail (Setaria viridis) | 3 | 4 | 0 3 | 0 4 | 1 | 2 | 4 |
|  | 1 | 3 | 0 2 | 2 | 1 | 2 | 4 |
| Nutsedge (Cyperus esculentus) | 3 | 0 | 0 1 | 0 0 | 0 | 0 | 0 |
|  | 1 | 0 | 0 0 | 0 | 0 | 0 | 0 |
| Shattercane (Sorghum bicolor) | 3 | 1 | 0 0 | 0 0 | 0 | 1 | 3 |
|  | 1 | 0 | 0 0 | 0 | 0 | 0 | 1 |
| Wild oats (Avena fatua) | 3 | 3 | 0 3 | 0 4 | 3 | 3 | 2 |
|  | 1 | 2 | 0 2 | 1 | 0 | 2 | 0 |
| Alfalfa (Medicago sativa) | 3 | 4 | 2 4 | 0 4 | 3 | 4 | 4 |
|  | 1 | 4 | 1 4 | 4 | 3 | 3 | 4 |
| Cotton (Gossypium herbaceum) | 3 | 1 | 0 2 | 0 4 | 0 | 4 | 4 |
|  | 1 | 1 | 0 1 | 4 | 0 | 4 | 3 |
| Peanuts (Arachis hypogaea) | 3 | 1 | 0 1 | 0 1 | 0 | 1 | 1 |
|  | 1 | 0 | 0 0 | 0 | 0 | 1 | 0 |
| Soybeans (Soja max) | 3 | 3 | 0 2 | 0 4 | 1 | 4 | 3 |
|  | 1 | 3 | 0 1 | 4 | 1 | 2 | 3 |
| Sugar beets (Beta vulgaris) | 3 | 4 | 0 4 | 0 3 | 3 | 4 | 4 |
|  | 1 | 4 | 0 4 | 3 | 3 | 4 | 4 |
| Tomato (Lycopersicum esculentum) | 3 | 4 | 0 4 | 0 4 | 1 | 4 | 4 |
|  | 1 | 2 | 0 2 | 3 | 1 | 4 | 4 |
| Corn (Zea mays) | 3 | 1 | 0 1 | 0 1 | 0 | 1 | 2 |
|  | 1 | 0 | 0 0 | 0 | 0 | 0 | 0 |
| Grain sorghum (Sorghum vulgare) | 3 | 1 | 0 0 | 0 0 | 0 | 1 | 3 |
|  | 1 | 0 | 0 0 | 0 | 0 | 0 | 2 |
| Rice (Oryza sativa) | 3 | 3 | 0 3 | 0 3 | 2 | — | 3 |
|  | 1 | 1 | 0 1 | 1 | 1 | — | 1 |
| Wheat (Tricium aestivum) | 3 | 3 | 0 2 | 0 3 | 2 | 2 | 2 |
|  | 1 | 1 | 0 1 | 0 | 0 | 1 | 0 |

-continued

Results of Pre- and Postemergent Use of Herbicides

| Compound No. Mode of Application Species | Appl'n. Rate (lb/A) | 74 Pre Post | | 75 Pre Post | | 76 Pre Post | | 77 Pre Post | | 78 Pre Post | | 79 Pre Post | |
|---|---|---|---|---|---|---|---|---|---|---|---|---|---|
| Cocklebur | 3 | 0 | 4 | | 4 | | 1 | | 4 | 4 | 0 | | 4 |
| (Xanthium pensylvanicum) | 1 | | 3 | | 4 | | 1 | | 4 | 4 | | | 2 |
| Lambsquarters | 3 | 4 | 4 | | 4 | | 4 | | 4 | 4 | 2 | | 4 |
| (Chenopodium album) | 1 | | 4 | | 4 | | 4 | | 3 | 4 | | | 4 |
| Morning glory | 3 | 0 | 3 | | 4 | | 1 | | 4 | 3 | 0 | | 4 |
| (Ipomea purpurea) | 1 | | 1 | | 2 | | 0 | | 4 | 2 | | | 1 |
| Pigweed | 3.3 | 4 | 2 | | 4 | | 4 | | 4 | 3 | 4 | | |
| (Amaranthus retroflexus) | 1 | | — | | 2 | | 3 | | 4 | 3 | | | 4 |
| Wild buckwheat | 3 | 0 | 4 | | 4 | | 4 | | 4 | 4 | 0 | | 4 |
| (Polygonum convolvulus)/1 | | 4 | 4 | | 2 | | 2 | | 3 | | 3 | | |
| Wild mustard | 3 | 1 | 4 | | 3 | | 4 | | 4 | 4 | 0 | | 2 |
| (Brassica kaber) | 1 | | — | | 2 | | 1 | | 2 | 3 | | | 0 |
| Barnyard grass | 3 | 0 | 2 | | 2 | | 1 | | — | 1 | 0 | | 1 |
| (Echinochloa crusgalli) | 1 | | 0 | | 0 | | 0 | | 1 | 0 | | | 1 |
| Crabgrass | 3 | 0 | 2 | | 1 | | 0 | | 2 | 1 | 1 | | 1 |
| (Digitaria sanquinalis) | 1 | | 0 | | 0 | | 0 | | 0 | 0 | | | 1 |
| Downey brome | 3 | 0 | 2 | | 0 | | 0 | | — | 1 | 0 | | 0 |
| (Bromus tectorum) | 1 | | 0 | | 0 | | 0 | | 0 | 1 | | | 0 |
| Giant foxtail | 3 | 0 | 1 | | 0 | | 0 | | 3 | 2 | 0 | | 2 |
| (Setaria faberii) | 1 | | 0 | | 0 | | 0 | | 0 | 1 | | | 1 |
| Green foxtail | 3 | 0 | 4 | | 3 | | 3 | | — | 4 | 0 | | 4 |
| (Setaria viridis) | 1 | | 2 | | 2 | | 0 | | 3 | 1 | | | 2 |
| Nutsedge | 3 | | 1 | | 0 | | 0 | | 1 | 0 | | | 0 |
| (Cyperus esculentus) | 1 | | 0 | | 0 | | 0 | | 0 | 0 | | | 0 |
| Shattercane | 3 | 0 | 0 | | 1 | | 0 | | — | 1 | 0 | | 1 |
| (Sorghum bicolor) | 1 | | 0 | | 0 | | 0 | | 0 | 0 | | | 0 |
| Wild oats | 3 | 0 | 4 | | 4 | | 1 | | — | 3 | 0 | | 2 |
| (Avena fatua) | 1 | | 1 | | 2 | | 0 | | 0 | 1 | | | 1 |
| Alfalfa | 3 | 1 | 4 | | 4 | | 3 | | 4 | 4 | 1 | | 4 |
| (Medicago sativa) | 1 | | 4 | | 4 | | 1 | | 4 | 3 | | | 3 |
| Cotton | 3 | 0 | 3 | | 4 | | 1 | | 4 | 3 | 0 | | 3 |
| (Gossypium herbaceum) | 1 | | 1 | | 2 | | 1 | | 4 | 2 | | | 1 |
| Peanuts | 3 | 0 | 1 | | 1 | | 0 | | 1 | 1 | 0 | | 1 |
| (Arachis hypogaea) | 1 | | 0 | | 1 | | 0 | | 1 | 1 | | | 0 |
| Soybeans | 3 | 0 | 4 | | 4 | | 3 | | 4 | 4 | 0 | | 3 |
| (Soja max) | 1 | | 3 | | 4 | | 0 | | 3 | 3 | | | 2 |
| Sugar beets | 3 | 0 | 4 | | 4 | | 3 | | 4 | 4 | 1 | | 4 |
| (Beta vulgaris) | 1 | | 3 | | 4 | | 3 | | 2 | 3 | | | 2 |
| Tomato | 3 | 0 | 3 | | 3 | | 3 | | 4 | 4 | 0 | | 4 |
| (Lycopersicum esculentum) | 1 | | 2 | | 2 | | 3 | | 4 | 3 | | | 3 |
| Corn | 3 | 0 | 1 | | 1 | | 1 | | — | 1 | 0 | | 1 |
| (Zea mays) | 1 | | 0 | | 0 | | 0 | | 0 | 0 | | | 0 |
| Grain sorghum | 3 | 0 | 0 | | 1 | | 0 | | — | 1 | 0 | | 1 |
| (Sorghum vulgare) | 1 | | 0 | | 0 | | 0 | | 0 | | 0 | | |
| Rice | 3 | 0 | 2 | | 2 | | 0 | | — | 2 | 0 | | 2 |
| (Oryza sativa) | 1 | | 2 | | 1 | | 0 | | 0 | 0 | | | 0 |
| Wheat | 3 | 0 | 4 | | 4 | | 1 | | — | 2 | 0 | | 3 |
| (Triticum aestivum) | 1 | | 1 | | 2 | | 0 | | 1 | 1 | | | 1 |

| Compound No. Mode of Application Species | Appl'n. Rate (lb/A) | 80 Pre Post | | 81 Pre Post | | 82 Pre Post | | 83 Pre Post | | 84 Pre Post | | 85 Pre Post | |
|---|---|---|---|---|---|---|---|---|---|---|---|---|---|
| Cocklebur | 3 | 0 | 4 | 0 | 4 | 4 | | 4 | | 4 | | | |
| (Xanthium pensylvanicum) | 1 | 0 | 4 | 0 | 4 | 4 | | 1 | | 4 | | | |
| Lambsquarters | 3 | 4 | 4 | 3 | 4 | 4 | | 4 | | 4 | | | |
| (Chenopodium album) | 1 | 4 | 4 | 3 | 4 | 4 | | 4 | | 4 | | | |
| Morning glory | 3 | 0 | 4 | 0 | 4 | 4 | | 4 | | 4 | | | |
| (Ipomea purpurea) | 1 | 0 | 3 | 0 | 3 | 3 | | 1 | | 4 | | | |
| Pigweed | 3 | 4 | 4 | 4 | 4 | 4 | | 4 | | 3 | | | |
| (Amaranthus retroflexus) | 1 | 4 | 4 | 3 | 4 | 4 | | 0 | | 0 | | | |
| Wild buckwheat | 3 | 0 | 4 | 0 | 4 | 4 | | 4 | | 4 | | | |
| (Polygonum convolvulus) | 1 | 0 | 4 | 0 | 4 | 4 | | 4 | | 4 | | | |
| Wild mustard | 3 | 4 | 4 | 3 | 4 | 4 | | 4 | | 4 | | | |
| (Brassica kaber) | 1 | 1 | 4 | 0 | 4 | 4 | | 3 | | 2 | | | |
| Barnyard grass | 3 | 1 | 1 | 0 | 2 | 2 | | 1 | | 1 | | | |
| (Echinochloa crusgalli) | 1 | 0 | 1 | 0 | 1 | 1 | | 0 | | 0 | | | |
| Crabgrass | 3 | 0 | 1 | 0 | 3 | 1 | | 3 | | 0 | | | |
| (Digitaria sanguinalis) | 1 | 0 | 1 | 0 | 2 | 1 | | 0 | | 0 | | | |
| Downey brome | 3 | 0 | 2 | 0 | 1 | 0 | | 2 | | 0 | | | |
| (Bromus tectorum) | 1 | 0 | 1 | 0 | 1 | 0 | | 0 | | 0 | | | |
| Giant foxtail | 3 | 0 | 2 | 0 | 3 | 2 | | 3 | | 0 | | | |
| (Setaria faberii) | 1 | 0 | 1 | 0 | 3 | 1 | | 0 | | 0 | | | |
| Green foxtail | 3 | 1 | 4 | 0 | 4 | 4 | | 1 | | 2 | | | |
| (Setaria viridis) | 1 | 0 | 3 | 0 | 3 | 1 | | 1 | | 0 | | | |
| Nutsedge | 3 | — | 0 | — | 0 | 0 | | — | | 0 | | | |
| (Cyperus esculentus) | 1 | — | 0 | — | 0 | 0 | | — | | 0 | | | |
| Shattercane | 3 | 0 | 2 | 0 | 1 | 1 | | 1 | | 0 | | | |

| Results of Pre- and Postemergent Use of Herbicides | | | | | | | | |
|---|---|---|---|---|---|---|---|---|
| (Sorghum bicolor) | 1 | 0 | 0 | 0 | 0 | 0 | 1 | 0 |
| Wild oats | 3 | 0 | 3 | 0 | 3 | 2 | 3 | 1 |
| (Avena fatua) | 1 | 0 | 1 | 0 | 2 | 1 | 2 | 0 |
| Alfalfa | 3 | 3 | 4 | 4 | 4 | 4 | 2 | 2 |
| (Medicago sativa) | 1 | 0 | 4 | 0 | 4 | 3 | 1 | 2 |
| Cotton | 3 | 0 | 3 | 0 | 3 | 4 | 1 | 1 |
| (Gossypium herbaceum) | 1 | 0 | 3 | 0 | 3 | 3 | 1 | 1 |
| Peanuts | 3 | 0 | 1 | 0 | 1 | 1 | 0 | 0 |
| (Arachis hypogaea) | 1 | 0 | 1 | 0 | 0 | 1 | 0 | 0 |
| Soybeans | 3 | 0 | 4 | 0 | 4 | 4 | 2 | 3 |
| (Soja max) | 1 | 0 | 3 | 0 | 4 | 3 | 1 | 2 |
| Sugar beets | 3 | 3 | 4 | 1 | 4 | 4 | 4 | 4 |
| (Beta vulgaris) | 1 | 2 | 4 | 0 | 4 | 4 | 4 | 2 |
| Tomato | 3 | 0 | 4 | 0 | 4 | 4 | 1 | 2 |
| (Lycopersicum esculentum) | 1 | 0 | 4 | 0 | 4 | 4 | 1 | 2 |
| Corn | 3 | 0 | 1 | 0 | 1 | 1 | 0 | 0 |
| (Zea mays) | 1 | 0 | 1 | 0 | 0 | 0 | 0 | 0 |
| Grain sorghum | 3 | 0 | 2 | 0 | 1 | 1 | 1 | 0 |
| (Sorghum vulgare) | 1 | 0 | 0 | 0 | 0 | 0 | 0 | 0 |
| Rice | 3 | 0 | 2 | 0 | 2 | 2 | 1 | 3 |
| (Oryza sativa) | 1 | 0 | 1 | 0 | 0 | 0 | 0 | 2 |
| Wheat | 3 | 0 | 3 | 0 | 2 | 1 | 2 | 1 |
| (Triticum aestivum) | 1 | 0 | 1 | 0 | 1 | 0 | 1 | 0 |

Use of the Novel Compounds as Fungicides

Following are illustrative procedures for use of the novel compounds as fungicides and assigning quantitative scores to observations.

In Vitro Fungicide Procedure

In each test, two bottles of modified potato dextrose broth containing the desired concentration of the novel compound (Selected from 25, 10, 3 and 1 ppm) were inoculated with spore suspensions, one with penicillium sp. and one with aspergillus sp. After two weeks the results were evaluated according to the following scale:
0 = maximum fungus growth
1 = fungus growth fair
2 = slight fungus growth
3 = only a trace of fungus growth
4 = no fungus growth

Foliar Fungicide Procedure

Solutions of each compound were prepared at concentrations of 300, 100 and 30 ppm and were then applied to fully expanded cucumber cotyledons by spraying with a pneumatic atomizing sprayer. After drying, the plants were placed in an inoculation chamber and were dusted with powdery mildew spores. The plants were maintained at a relative humidity of 90 to 100% for 24 hours and were then removed to a greenhouse. Results were observed after 10 to 14 days and disease control was rated according to the following scale:
0 = no control
1 = poor control
2 = moderate control
3 = good control
4 = complete control

Soil Fungicide Procedure

Each novel compound was formulated with attaclay at a concentration of 20 percent by weight. The treated clay was then incorporated into containers of soil inoculated with rhizoctonia solani, at a concentration of the test compound of 75, 100, 50 and 25 ppm. Ten cotton seeds were planted in each container of soil. After three weeks the results were observed and rated according to the following schedule.

Emergence (E)

0 = no emergence
1 = 1 to 3 plants emerged
2 = 4 to 6 plants emerged
3 = 7 to 9 plants emerged
4 = 10 plants emerged

Disease Control (D)

0 = all plants diseased
1 = 1-30 percent healthy plants
2 = 31-60 percent healthy plants
3 = 61-90 percent healthy plants
4 = all plants healthy Illustrative results of use of the novel compounds as fungicides are tabulated below.

| Results of Fungicidal Use | | | | | |
|---|---|---|---|---|---|
| Compound No. | Con'n. ppm | In Vitro | Foliar | Soil(E) | (D) |
| 37 | 300 | | 4 | | |
|  | 100 | | 3 | | |
| 55 | 75 | | | 2 | 0 |
| 56 | 100 | | 2 | | |
| 57 | 30 | | 2 | | |
| 59 | 300 | 4 | 4 | | |
|  | 100 | | 3 | | |
|  | 30 | | 4 | | |
| 63 | 100 | 1 | | | |
|  | 30 | | 1 | | |
| 66 | 25 | | 1 | | |
|  |  | 2 | | | |
|  | 300 | | 2 | | |
| 12 | 100 | | | 4 | 0 |
| 7 | 100 | | 3 | | |
| 16 | 75 | | | 4 | 0 |
| 25 | 75 | | | 4 | 1 |

The novel compounds disclosed herein are useful in agriculture in various situations. For example, compounds numbered 26 and 27 are particularly useful in control of undesired broadleaf vegetation, while compounds numbered 32, 38, 40, 41, 42 and 43 are useful in combating both broadleaf weeds and noxious grasses.

Compound number 32 is specifically suitable for combating shattercane in maize (corn) fields. Compound number 49 may be used to control both broadleaf weeds and wild oats in wheat. Compounds numbered 37 and 59 are particularly useful as agricultural fungicides. It appears to be possible that selective herbicidal action in some instances is enhanced by protection of the crop plants to some extent from fungus infestation. This may occur to some extent by lessening the tendency of dead rotting weeds to become reservoirs of fungus disease. The tabulated data herein will serve as a guide to the skilled worker in deciding upon an effective amount of herbicide to apply in each crop and weed situation. The ideal application rate will, of course vary with the crop, soil and weather, as is well understood by workers in the art.

I claim:
1. A compound of the formula

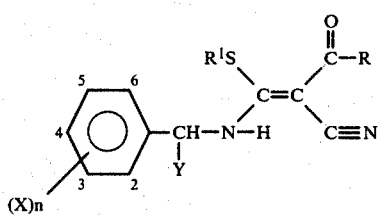

in which R is $C_1$ to $C_4$ straight chain saturated or unsaturated alkoxy, amino, dimethylamino or straight chain $C_1$ to $C_3$ monoalkylamino, $R^1$ is methyl or ethyl, X is nitro, methoxy, methyl, ethyl, Br, Cl, or F in which n is an integer from 0 to 2, at least one of the 2 and 6 positions is unsubstituted and Y is H or a $C_1$ to $C_5$ branched or unbranched, saturated or unsaturated alkyl or cycloalkyl substitutent group.

2. 2-Cyano-3-(para-fluoro-alpha-methylbenzylamino)-3-ethylthioacrylamide.

3. 2-Cyano-3-(p-chloro-alpha-methylbenzylamino)-3-ethylthioacrylamide.

4. 2-Cyano-3-(3-fluorobenzylamino)-3-methylthioacrylamide.

5. 2-Cyano-3-(3'-fluoro-alpha-methylbenzylamino)-3-methylthioacrylamide.

6. 3-(4-Chloro-alpha-ethylbenzylamino)-2-cyano-3-methylthioacrylamide.

7. 2-Cyano-3-(4'-fluoro-alpha-ethylbenzylamino)-3-methylthioacrylamide.

8. Methyl 2-cyano-3-(para-methyl-alpha-methylbenzylamino)-3-methylthioacrylamide.

9. Methyl 2-cyano-3-(3,4-dichloro-alpha-methylbenzylamino)-3-methylthioacrylate.

10. Methyl 2-cyano-3-(meta-fluorobenzylamino)-3-methylthioacrylate.

11. Methyl 2-cyano-3-(meta-methylbenzylamino)-3-methylthioacrylate.

12. Methyl 3-(para-chloro-alpha-ethylbenzylamino)-2-cyano-3-methylthioacrylate.

13. Methyl 3-(para-bromo-alpha-ethylbenzylamino)-2-cyano-3-methylthioacrylate.

14. Methyl 2-cyano-3-(alpha-ethyl-para-fluorobenzylamino)-3-methylthioacrylate.

15. Methyl 2-cyano-3-(3'-methyl-alpha-methylbenzylamino)-3-methylthioacrylate.

16. Ethyl 3-(4'-chloro-alpha-methylbenzylamino)-2-cyano-3-methylthioacrylate.

17. Ethyl 2-cyano-3-(4'-fluro-alpha-methylbenzylamino)-3-methylthioacrylate.

18. Ethyl 2-cyano-3-(3',4'-dichloro-alpha-methylbenzylamino)-3-methylthioacrylate.

19. Ethyl 2-cyano-3-(4'-fluoro-alpha-methylbenzylamino)-3-methylthioacrylate.

20. Ethyl 3-(4'-chloro-alpha-ethylbenzylamino)-2-cyano-3-methylthioacrylate.

21. Ethyl 3-(4-bromo-alpha-ethylbenzylamino)-2-cyano-3-methylthioacrylate.

22. Ethyl 2-cyano-3-(3',4'-dichlorobenzylamino)-3-methylthioacrylate.

23. Ethyl 3-(4'-bromo-alpha-methylbenzylamino)-2-cyanomethylthioacrylamide.

24. Allyl 3-(3-chlorobenzylamino)-2-cyano-3-methylthioacrylate.

25. Allyl 2-cyano-3-(4-fluoro-alpha-methylbenzylamino)-3-methylthioacrylate.

26. Allyl 2-cyano-3-(4-fluoro-alpha-ethylbenzylamino-3-methylthioacrylate.

27. Allyl 3-(4'chloro-alpha-ethylbenzylamino)-2-cyano-3-methylthioacrylate.

28. Normal-butyl 2-cyano-3-(3',4'-dichlorobenzylamino)-3-methylthioacrylate.

29. The method of combating unwanted vegetation either pre- or post-emergently comprising applying a herbicidally effective amount of a compound of claim 2, 3, 4, 5, 6, 7, 8, 9, 10, 11, 12, 13, 14, 15, 16, 17, 18, 19, 20, 21, 22, 23, 24, 25, 26, 27, or 28, in combination with an inert carrier.

* * * * *

UNITED STATES PATENT OFFICE
CERTIFICATE OF CORRECTION

Patent No. 4,201,569                    Dated May 6, 1980

Inventor(s) Loren W. Hedrich

It is certified that error appears in the above-identified patent and that said Letters Patent are hereby corrected as shown below:

Column 5, No. 84, in the table, (X)n should read---3,4-dichloro----

Column 6, line 49, should read---plant seeds and were then covered with about 1/4 inch of---

Column 7, line 19, Species column, should read---(Sorghum bicolor)---

Additional corrections in tables:

Column 7 & 8

| | Appl'n. Rate (lb/A) | 26 Pre | 26 Post | 27 Pre | 27 Post | 28 Pre | 28 Post | 29 Pre | 29 Post | 30 Pre | 30 Post | 31 Pre | 31 Post |
|---|---|---|---|---|---|---|---|---|---|---|---|---|---|
| Alfalfa | 3 | 2 | | 1 | 4 | 3 | | 4 | 4 | 4 | 4 | 4 | |
| (Medicago sativa) | 1 | | 4 | | 4 | 2 | | 4 | 4 | 4 | 4 | - | |
| Peanuts | 3 | 0 | | 0 | 1 | 0 | | 0 | | - | 1 | 0 | |
| (Arachis hypogaea) | 1 | | 1 | | 1 | 0 | | 0 | 0 | 0 | 0 | 0 | |
| Rice | 3 | 0 | | 0 | 2 | 1 | | 0 | 2 | 0 | 1 | 1 | |

| | | Compound No. 32 | | Compound No. 33 | | Compound No. 34 | | Compound No. 35 | | Compound No. 36 | | Compound No. 37 | |
|---|---|---|---|---|---|---|---|---|---|---|---|---|---|
| Green Foxtail | 3 | | | | | | | 3 | | | | | |
| (Soja max) | 1 | 0 | 4 | 0 | 3 | 0 | 1 | 2 | | 3 | | 0 | 4 |
| Sugar Beets | 3 | 1 | 4 | 3 | 4 | 3 | 3 | 4 | | 2 | 4 | 4 | 4 |
| (Lycopersicum esculentum) | 1 | 0 | 3 | 0 | 3 | 0 | 1 | 3 | | 1 | | 2 | 3 |

UNITED STATES PATENT OFFICE
CERTIFICATE OF CORRECTION

Patent No. 4,201,569  Dated May 6, 1980

Inventor(s) Loren W. Hedrich

It is certified that error appears in the above-identified patent and that said Letters Patent are hereby corrected as shown below:

| | Appl'n. Rate (lb/A) | 32 PrePost | 33 PrePost | 34 PrePost | 35 PrePost | 36 PrePost | 37 PrePost |
|---|---|---|---|---|---|---|---|
| Column 9 & 10 | | | | | | | |
| (Sorghum vulgare) | 1 | 0  3 | 0  0 | 0  0 | 0 | 0 | 0  0 |

| | | 38 | 39 | 40 | 41 | 42 | 43 |
|---|---|---|---|---|---|---|---|
| Cocklebur | 3 | 0  4 | 0  4 | 0  4 | -  4 | 0  4 | 4 |
| (Xanthium pensyl-vanicum) | 1 | 0  4 | 0  4 | 4 | -  - | -  - | 4 |
| (Tricicum aestivum) | | | | | | | |

| | | 44 | 45 | 46 | 47 | 48 | 49 |
|---|---|---|---|---|---|---|---|
| Barnyard grass | 3 | 0  2 | 3  3 | 2  3 | 3 | 2  2 | 3 |
| Column 11 & 12 | | 50 | 51 | 52 | 53 | 54 | 55 |
| Grain sorghum (Sorghum vulgare) | 1 | 0  0 | 0  2 | 0 | 0 | 0 | 0  0 |
| Column 13 & 14 | | | | | | | |
| Wheat (Triticum aestivum) | | 62 | 63 | 64 | 65 | 66 | 67 |
| Pigweed | 3 | 3  2 | 3  4 | 3  3 | 3  2 | 3  3 | 3  4 |
| (Bromus tectorum) | 1 | 0  0 | 0  0 | 0  0 | 0  1 | 0  0 | 0  0 |
| (Setaria faberii) | 1 | 0  1 | 0  0 | 0  0 | 2  0 | 0  0 | 0  0 |

UNITED STATES PATENT OFFICE
CERTIFICATE OF CORRECTION

Patent No. 4,201,569    Dated May 6, 1980

Inventor(s) Loren W. Hedrich

It is certified that error appears in the above-identified patent and that said Letters Patent are hereby corrected as shown below:

Column 15 & 16

|  | Appl/n. Rate (lb/A) | 62 Pre Post | 63 Pre Post | 64 Pre Post | 65 Pre Post | 66 Pre Post | 67 Pre Post |
|---|---|---|---|---|---|---|---|
| Nutsedge (Cyperus esculentus) | 3 | 0  2 | 0  0 | 0  0 | 0  0 | 0  1 | 0  0 |
|  | 1 | 0  1 | 0  0 | 0  0 | 0  0 | 0  0 | 0  0 |
| (Lycopersicum esculentum) | 1 | 1  3 | 0  4 | 0  3 | 0  3 | 0  2 | 1  3 |
| Rice (Oryza sativa) | 3 | 0  1 | 0  2 | 0  1 | 0  2 | 0  4 | 0  2 |
|  | 1 | 0  1 | 0  1 | 0  0 | 0  1 | 0  1 | 0  1 |

UNITED STATES PATENT OFFICE
CERTIFICATE OF CORRECTION

Patent No. 4,201,569          Dated May 6, 1980

Inventor(s) Loren W. Hedrich

It is certified that error appears in the above-identified patent and that said Letters Patent are hereby corrected as shown below:

| | | 74 | 75 | 76 | 77 | 78 | 79 |
|---|---|---|---|---|---|---|---|
| (Triticum aestivum) Column 17 & 18 | | | | | | | |
| Pigweed | 3 | 3  4 | 2 | 4 | 4 | 4  3 | 4 |
| (Polygonum convol- vulus) | 1 | 4 | 4 | 2 | 2 | 3 | 3 |
| (Sorghum vulgare) | 1 | 0 | 0 | 0 | 0 | 0 | 0 |

| | | 80 | 81 | 82 | 83 | 84 | 85 |
|---|---|---|---|---|---|---|---|
| Column 19 & 20 | | | | | | | |
| Tomato | 3 | 0  4 | 0  4 | 4 | 4 | 4 | 3 |

Column 20, line 51, Compound 59, delete the "4" in the In Vitro column.
line 54, Compound 63, delete the "1" in the In Vitro column and add --1-- to the Foliar column.
line 57, Compound 66, add --2-- to In Vitro and delete "1" in Foliar column.

Signed and Sealed this

Twenty-eighth Day of October 1980

[SEAL]

Attest:

SIDNEY A. DIAMOND

Attesting Officer

Commissioner of Patents and Trademarks